US009387048B2

(12) United States Patent
Donhowe et al.

(10) Patent No.: US 9,387,048 B2
(45) Date of Patent: Jul. 12, 2016

(54) CATHETER SENSOR SYSTEMS

(75) Inventors: Caitlin Q. Donhowe, Sunnyvale, CA (US); Vincent Duindam, Mountain View, CA (US); Giuseppe Maria Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 490 days.

(21) Appl. No.: 13/274,237

(22) Filed: Oct. 14, 2011

(65) Prior Publication Data

US 2013/0096572 A1    Apr. 18, 2013

(51) Int. Cl.
*A61B 5/05* (2006.01)
*A61B 19/00* (2006.01)

(52) U.S. Cl.
CPC ..... *A61B 19/5244* (2013.01); *A61B 2019/2215* (2013.01); *A61B 2019/5251* (2013.01); *A61B 2019/5261* (2013.01); *A61B 2034/302* (2016.02)

(58) Field of Classification Search
CPC ............... A61B 19/2544; A61B 2019/5251
USPC ........................................................ 600/424
See application file for complete search history.

(56) References Cited

U.S. PATENT DOCUMENTS

| 3,096,962 A | 7/1963 | Meijs |
| 3,546,961 A | 12/1970 | Marton |
| 4,437,114 A | 3/1984 | LaRussa |
| 4,792,715 A | 12/1988 | Barsky et al. |
| 4,809,191 A | 2/1989 | Domeier et al. |
| 4,905,082 A | 2/1990 | Nishigaki et al. |
| 4,949,927 A | 8/1990 | Madocks et al. |
| 5,114,403 A | 5/1992 | Clarke et al. |
| 5,174,276 A | 12/1992 | Crockard |
| 5,251,611 A | 10/1993 | Zehel et al. |
| 5,297,536 A | 3/1994 | Wilk |
| 5,307,437 A | 4/1994 | Facq et al. |
| 5,417,210 A | 5/1995 | Funda et al. |
| 5,429,604 A | 7/1995 | Hammersmark et al. |
| 5,487,757 A | 1/1996 | Truckai et al. |
| 5,588,949 A | 12/1996 | Taylor et al. |
| 5,617,515 A | 4/1997 | MacLaren et al. |
| 5,624,380 A | 4/1997 | Takayama et al. |

(Continued)

FOREIGN PATENT DOCUMENTS

| JP | S57190549 A | 11/1982 |
| JP | H06285009 A | 10/1994 |

(Continued)

OTHER PUBLICATIONS

International Search Report and Written Opinion for Application No. PCT/US2012/059889, mailed on Mar. 29, 2013, 14 pages.

(Continued)

*Primary Examiner* — Patricia Park

(57) ABSTRACT

A medical system including a catheter or other flexible structure uses a combination of two different sensor systems to measure a pose of a section or tip of the catheter or flexible structure. The first sensor system, which may include an electromagnetic sensor, can measure a pose of a first section of the catheter, and the second sensor system can measure a pose of the second section relative to the first section. The second sensor system may employ a technology such as fiber shape sensing that permits the second section to be smaller than the first section, so that a distal tip of the catheter or flexible structure can fit within smaller natural lumens.

19 Claims, 4 Drawing Sheets

(56) References Cited

U.S. PATENT DOCUMENTS

| | | |
|---|---|---|
| 5,729,129 A | 3/1998 | Acker |
| 5,752,112 A | 5/1998 | Paddock et al. |
| 5,755,713 A | 5/1998 | Bilof et al. |
| 5,759,151 A | 6/1998 | Sturges |
| 5,792,135 A | 8/1998 | Madhani et al. |
| 5,797,900 A | 8/1998 | Madhani et al. |
| 5,817,084 A | 10/1998 | Jensen |
| 5,855,569 A | 1/1999 | Komi |
| 5,868,760 A | 2/1999 | McGuckin, Jr. |
| 5,876,325 A | 3/1999 | Mizuno et al. |
| 5,892,860 A | 4/1999 | Maron et al. |
| 5,899,425 A | 5/1999 | Corey Jr. et al. |
| 5,976,071 A | 11/1999 | Sekiya |
| 5,982,791 A | 11/1999 | Sorin et al. |
| 6,013,024 A | 1/2000 | Mitsuda et al. |
| 6,030,130 A | 2/2000 | Paddock et al. |
| 6,066,090 A | 5/2000 | Yoon |
| 6,120,433 A | 9/2000 | Mizuno et al. |
| 6,132,368 A | 10/2000 | Cooper |
| 6,161,032 A | 12/2000 | Acker |
| 6,171,277 B1 | 1/2001 | Ponzi |
| 6,188,355 B1 | 2/2001 | Gilboa |
| 6,191,414 B1 | 2/2001 | Ogle et al. |
| 6,200,274 B1 | 3/2001 | McNeirney |
| 6,203,493 B1 | 3/2001 | Ben-Haim |
| 6,253,770 B1 | 7/2001 | Acker et al. |
| 6,275,628 B1 | 8/2001 | Jones et al. |
| 6,331,181 B1 | 12/2001 | Tierney et al. |
| 6,332,089 B1 | 12/2001 | Acker et al. |
| 6,335,617 B1 | 1/2002 | Osadchy et al. |
| 6,347,892 B1 | 2/2002 | Paddock et al. |
| 6,352,503 B1 | 3/2002 | Matsui et al. |
| 6,366,722 B1 | 4/2002 | Murphy et al. |
| 6,366,799 B1 | 4/2002 | Acker et al. |
| 6,371,952 B1 | 4/2002 | Madhani et al. |
| 6,380,732 B1 | 4/2002 | Gilboa |
| 6,389,187 B1 | 5/2002 | Greenaway et al. |
| 6,396,574 B1 | 5/2002 | Lee et al. |
| 6,432,041 B1 | 8/2002 | Taniguchi et al. |
| 6,441,577 B2 | 8/2002 | Blumenkranz et al. |
| 6,451,027 B1 | 9/2002 | Cooper et al. |
| 6,453,190 B1 | 9/2002 | Acker et al. |
| 6,470,205 B2 | 10/2002 | Bosselmann et al. |
| 6,471,710 B1 | 10/2002 | Bucholtz |
| 6,478,028 B1 | 11/2002 | Paolitto et al. |
| 6,484,118 B1 | 11/2002 | Govari |
| 6,487,352 B1 | 11/2002 | Sobiski et al. |
| 6,490,467 B1 | 12/2002 | Bucholz et al. |
| 6,554,793 B1 | 4/2003 | Pauker et al. |
| 6,571,639 B1 | 6/2003 | May et al. |
| 6,572,629 B2 | 6/2003 | Kalloo et al. |
| 6,574,355 B2 | 6/2003 | Green |
| 6,575,644 B2 | 6/2003 | Paddock et al. |
| 6,578,967 B1 | 6/2003 | Paddock et al. |
| 6,618,612 B1 | 9/2003 | Acker et al. |
| 6,645,196 B1 | 11/2003 | Nixon et al. |
| 6,648,816 B2 | 11/2003 | Irion et al. |
| 6,671,055 B1 | 12/2003 | Wavering et al. |
| 6,671,581 B2 | 12/2003 | Niemeyer et al. |
| 6,720,988 B1 | 4/2004 | Gere et al. |
| 6,743,239 B1 | 6/2004 | Kuehn et al. |
| 6,758,843 B2 | 7/2004 | Jensen |
| 6,783,491 B2 | 8/2004 | Saadat et al. |
| 6,790,173 B2 | 9/2004 | Saadat et al. |
| 6,817,974 B2 | 11/2004 | Cooper et al. |
| 6,833,814 B2 | 12/2004 | Gilboa et al. |
| 6,837,847 B2 | 1/2005 | Ewers et al. |
| 6,866,671 B2 | 3/2005 | Tierney et al. |
| 6,902,560 B1 | 6/2005 | Morley et al. |
| 6,936,042 B2 | 8/2005 | Wallace et al. |
| 6,942,613 B2 | 9/2005 | Ewers et al. |
| 6,960,162 B2 | 11/2005 | Saadat et al. |
| 6,960,163 B2 | 11/2005 | Ewers et al. |
| 6,984,203 B2 | 1/2006 | Tartaglia et al. |
| 6,991,602 B2 | 1/2006 | Nakazawa et al. |
| 6,994,703 B2 | 2/2006 | Wang et al. |
| 6,997,870 B2 | 2/2006 | Couvillon, Jr. |
| 7,007,699 B2 | 3/2006 | Martinelli et al. |
| 7,041,052 B2 | 5/2006 | Saadat et al. |
| 7,042,573 B2 | 5/2006 | Froggatt |
| 7,090,637 B2 | 8/2006 | Danitz et al. |
| 7,090,683 B2 | 8/2006 | Brock et al. |
| 7,128,708 B2 | 10/2006 | Saadat et al. |
| 7,139,601 B2 | 11/2006 | Bucholz et al. |
| 7,197,354 B2 | 3/2007 | Sobe |
| 7,252,660 B2 | 8/2007 | Kunz |
| 7,277,120 B2 | 10/2007 | Gere et al. |
| 7,320,700 B2 | 1/2008 | Cooper et al. |
| 7,371,028 B2 | 5/2008 | Gordon et al. |
| 7,398,116 B2 | 7/2008 | Edwards |
| 7,594,912 B2 | 9/2009 | Cooper et al. |
| 7,715,105 B2 | 5/2010 | Forkey et al. |
| 7,720,322 B2 | 5/2010 | Prisco |
| 7,725,214 B2 | 5/2010 | Diolaiti |
| 7,853,307 B2 | 12/2010 | Edwards |
| 7,920,909 B2 | 4/2011 | Lyon et al. |
| 7,922,650 B2 | 4/2011 | McWeeney et al. |
| 7,930,065 B2 | 4/2011 | Larkin et al. |
| 7,947,000 B2 | 5/2011 | Vargas et al. |
| 7,962,193 B2 | 6/2011 | Edwards et al. |
| 8,016,749 B2 | 9/2011 | Clerc et al. |
| 8,784,303 B2 | 7/2014 | Laby et al. |
| 8,784,435 B2 | 7/2014 | Cooper et al. |
| 9,060,678 B2 | 6/2015 | Larkin et al. |
| 2001/0049509 A1 | 12/2001 | Sekine et al. |
| 2002/0087169 A1 | 7/2002 | Brock et al. |
| 2002/0120252 A1 | 8/2002 | Brock et al. |
| 2002/0143319 A1 | 10/2002 | Brock |
| 2002/0173786 A1 | 11/2002 | Kortenbach et al. |
| 2003/0050649 A1 | 3/2003 | Brock et al. |
| 2003/0236455 A1 | 12/2003 | Swanson et al. |
| 2003/0236505 A1 | 12/2003 | Bonadio et al. |
| 2004/0054355 A1 | 3/2004 | Gerbi et al. |
| 2004/0083808 A1 | 5/2004 | Rambow et al. |
| 2004/0138525 A1 | 7/2004 | Saadat et al. |
| 2004/0138529 A1 | 7/2004 | Wiltshire et al. |
| 2004/0153191 A1 | 8/2004 | Grimm et al. |
| 2004/0202400 A1 | 10/2004 | Kochergin et al. |
| 2005/0004431 A1 | 1/2005 | Kogasaka et al. |
| 2005/0043718 A1 | 2/2005 | Madhani et al. |
| 2005/0049486 A1* | 3/2005 | Urquhart et al. ............ 600/429 |
| 2005/0059960 A1 | 3/2005 | Simaan et al. |
| 2005/0065397 A1 | 3/2005 | Saadat et al. |
| 2005/0065398 A1 | 3/2005 | Adams |
| 2005/0096502 A1 | 5/2005 | Khalili |
| 2005/0102062 A1 | 5/2005 | Green |
| 2005/0131343 A1 | 6/2005 | Abrams et al. |
| 2005/0197536 A1 | 9/2005 | Banik et al. |
| 2005/0197557 A1 | 9/2005 | Strommer et al. |
| 2005/0215983 A1 | 9/2005 | Brock |
| 2005/0222554 A1 | 10/2005 | Wallace et al. |
| 2005/0251176 A1 | 11/2005 | Swanstrom et al. |
| 2005/0272977 A1 | 12/2005 | Saadat et al. |
| 2005/0284221 A1 | 12/2005 | Danisch et al. |
| 2006/0013523 A1 | 1/2006 | Childers et al. |
| 2006/0025652 A1 | 2/2006 | Vargas |
| 2006/0149418 A1 | 7/2006 | Anvari |
| 2006/0161136 A1 | 7/2006 | Anderson et al. |
| 2007/0021738 A1 | 1/2007 | Hasser et al. |
| 2007/0055128 A1* | 3/2007 | Glossop ..................... 600/407 |
| 2007/0055291 A1 | 3/2007 | Birkmeyer et al. |
| 2007/0065077 A1 | 3/2007 | Childers et al. |
| 2007/0089557 A1 | 4/2007 | Solomon et al. |
| 2007/0106116 A1* | 5/2007 | Sugimoto .................... 600/117 |
| 2007/0135803 A1 | 6/2007 | Belson |
| 2007/0137371 A1 | 6/2007 | Devengenzo et al. |
| 2007/0151391 A1 | 7/2007 | Larkin et al. |
| 2007/0156020 A1 | 7/2007 | Foley et al. |
| 2007/0173694 A1 | 7/2007 | Tsuji et al. |
| 2007/0197896 A1 | 8/2007 | Moll et al. |
| 2007/0225554 A1 | 9/2007 | Maseda et al. |
| 2007/0225559 A1* | 9/2007 | Clerc et al. ................. 600/117 |
| 2007/0265503 A1 | 11/2007 | Schlesinger et al. |
| 2007/0283970 A1 | 12/2007 | Mohr et al. |

(56) References Cited

U.S. PATENT DOCUMENTS

| | | |
|---|---|---|
| 2007/0287884 A1 | 12/2007 | Schena |
| 2007/0287889 A1 | 12/2007 | Mohr |
| 2007/0287992 A1 | 12/2007 | Diolaiti et al. |
| 2008/0058861 A1 | 3/2008 | Cooper et al. |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065106 A1 | 3/2008 | Larkin |
| 2008/0065107 A1 | 3/2008 | Larkin et al. |
| 2008/0065109 A1 | 3/2008 | Larkin |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0103362 A1 | 5/2008 | Couvillon, Jr. |
| 2008/0147089 A1 | 6/2008 | Loh et al. |
| 2008/0151041 A1 | 6/2008 | Shafer et al. |
| 2008/0156971 A1 | 7/2008 | Ogisu et al. |
| 2008/0212082 A1 | 9/2008 | Froggatt et al. |
| 2008/0255505 A1 | 10/2008 | Carlson et al. |
| 2008/0287963 A1 | 11/2008 | Rogers et al. |
| 2009/0085807 A1* | 4/2009 | Anderson ............ 342/450 |
| 2009/0088756 A1* | 4/2009 | Anderson ............ 606/80 |
| 2009/0096443 A1* | 4/2009 | Anderson ............ 324/207.17 |
| 2009/0123111 A1 | 5/2009 | Udd |
| 2009/0137952 A1* | 5/2009 | Ramamurthy et al. .... 604/95.01 |
| 2009/0248040 A1 | 10/2009 | Cooper et al. |
| 2009/0281566 A1 | 11/2009 | Edwards et al. |
| 2009/0314131 A1 | 12/2009 | Bailey |
| 2009/0322001 A1 | 12/2009 | Luke et al. |
| 2009/0326322 A1 | 12/2009 | Diolaiti |
| 2009/0326552 A1 | 12/2009 | Diolaiti |
| 2009/0326553 A1 | 12/2009 | Mustufa et al. |
| 2010/0076303 A1 | 3/2010 | McKinley |
| 2010/0082041 A1 | 4/2010 | Prisco |
| 2010/0170519 A1 | 7/2010 | Romo et al. |
| 2010/0210939 A1 | 8/2010 | Hartmann et al. |
| 2010/0222647 A1 | 9/2010 | Hashimshony et al. |
| 2010/0274087 A1 | 10/2010 | Diolaiti et al. |
| 2010/0331820 A1 | 12/2010 | Prisco et al. |
| 2010/0332033 A1 | 12/2010 | Diolaiti et al. |
| 2011/0028991 A1 | 2/2011 | Ikeda et al. |
| 2011/0040305 A1 | 2/2011 | Gomez et al. |
| 2011/0040404 A1 | 2/2011 | Diolaiti et al. |
| 2011/0054309 A1 | 3/2011 | Edwards |
| 2011/0082365 A1 | 4/2011 | McGrogan et al. |
| 2011/0152879 A1 | 6/2011 | Williams |
| 2011/0172680 A1* | 7/2011 | Younge et al. ............ 606/130 |
| 2011/0184241 A1 | 7/2011 | Zubiate et al. |
| 2011/0184276 A1 | 7/2011 | Lyon et al. |
| 2011/0196419 A1 | 8/2011 | Cooper |
| 2011/0201883 A1 | 8/2011 | Cooper et al. |
| 2011/0201922 A1* | 8/2011 | Hezemans et al. ............ 600/424 |
| 2011/0202068 A1 | 8/2011 | Diolaiti et al. |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0237889 A1 | 9/2011 | Tanaka |
| 2011/0277576 A1 | 11/2011 | Cooper |
| 2011/0277579 A1 | 11/2011 | Anderson et al. |
| 2011/0277580 A1 | 11/2011 | Cooper et al. |
| 2011/0277775 A1 | 11/2011 | Holop et al. |
| 2011/0277776 A1 | 11/2011 | McGrogan et al. |
| 2011/0282356 A1 | 11/2011 | Solomon et al. |
| 2011/0282357 A1 | 11/2011 | Rogers et al. |
| 2011/0282358 A1 | 11/2011 | Gomez et al. |
| 2011/0282359 A1 | 11/2011 | Duval |
| 2011/0282491 A1 | 11/2011 | Prisco et al. |
| 2012/0010628 A1 | 1/2012 | Cooper et al. |
| 2012/0046522 A1 | 2/2012 | Naito |
| 2012/0123441 A1 | 5/2012 | Au et al. |
| 2012/0165608 A1 | 6/2012 | Banik et al. |
| 2013/0096377 A1 | 4/2013 | Duindam et al. |
| 2013/0096385 A1 | 4/2013 | Fenech et al. |
| 2013/0096497 A1 | 4/2013 | Duindam et al. |
| 2013/0144124 A1 | 6/2013 | Prisco et al. |
| 2013/0169272 A1 | 7/2013 | Eichler et al. |
| 2013/0172906 A1 | 7/2013 | Olson et al. |
| 2013/0303944 A1 | 11/2013 | Duindam |
| 2014/0296872 A1 | 10/2014 | Cooper et al. |

FOREIGN PATENT DOCUMENTS

| | | |
|---|---|---|
| JP | H07504363 A | 5/1995 |
| JP | 2000093522 A | 4/2000 |
| JP | 2000166936 A | 6/2000 |
| JP | 2003275223 A | 9/2003 |
| KR | 19990087101 A | 12/1999 |
| WO | WO-9313916 A1 | 7/1993 |
| WO | WO-9605768 A1 | 2/1996 |
| WO | WO-9729690 A1 | 8/1997 |
| WO | WO-0051486 A1 | 9/2000 |
| WO | 0207809 A1 | 1/2002 |
| WO | 2004016155 A2 | 2/2004 |
| WO | WO-2005087128 A1 | 9/2005 |
| WO | WO-2006039092 A2 | 4/2006 |
| WO | 2007109418 A2 | 9/2007 |
| WO | WO-2007146987 A2 | 12/2007 |
| WO | WO-2008028149 A2 | 3/2008 |
| WO | WO-2009002701 A2 | 12/2008 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Shang, J. et al., "An Articulated Universal Joint Based Flexible Access Robot for Minimally Invasive Surgery," 2011 IEEE Conference on Robotics and Automation (ICRA), May 9-13, 2011, London, UK, pp. 1147-1152.

Olympus Medical Systems, "Olympus ScopeGuide Receives FDA Clearance," Press Release dated May 24, 2011, 2 pages.

Abbott, Daniel J. et al., "Design of an Endoluminal NOTES Robotic System," Conference on Intelligent Robots and Systems, 2007, pp. 410-416.

Anisfield, Nancy; "Ascension Technology Puts Spotlight on DC Field Magnetic Motion Tracking," HP Chronicle, Aug. 2000, vol. 17, No. 9, 3 Pages.

Ascari, Luca et al., "A New Active Microendoscope for Exploring the Sub-Arachnoid Space in the Spinal Cord," Proc. IEEE International Conference on Robotics and Automation, 2003, pp. 2657-2662, vol. 2, IEEE.

Barnes Industries, Inc., "How a Ball Screw Works," 4 pages, Copyright 2007; Internet: http://www.barnesballscrew.com/ball.htm.

Berthold III, John W., "Historical Review of Microbend Fiber-Optic Sensors," Journal of Lightwave Technology, vol. 13, No. 7, Jul. 1995, pp. 1193-1199.

Blue Road Research, "Overview of Fiber Optic Sensors," 40 pages, first posted Dec. 8, 2004. Internet &It;www.bluerr.com/papers/Overview_of_FOS2.pdf>.

Cao, Caroline G.L., "Designing Spatial Orientation in Endoscopic Environments," Proceedings of the Human Factors and Ergonomics Society 45th Annual Meeting, 2001, pp. 1259-1263.

Cao, Caroline G.L., "Disorientation in Minimal Access Surgery: A Case Study," Proceedings of the IEA 2000/HFES 2000 Congress, pp. 4-169-4-172.

(56) References Cited

OTHER PUBLICATIONS

Childers, Brooks A., et al., "Use of 3000 Bragg grating strain sensors distributed on four eight-meter optical fibers during static load tests of a composite structure," SPIE 8th International Symposium on Smart Structures and Materials, Mar. 4-8, 2001, Newport Beach, California, 10 Pages.
Choi, Dong-Geol et al., "Design of a Spring Backbone Micro Endoscope," Conference on Intelligent Robots and Systems, 2007, pp. 1815-1821.
U.S. Appl. No. 11/762,185, filed Jun. 13, 2007.
U.S. Appl. No. 60/813,028, filed Jun. 13, 2006.
U.S. Appl. No. 60/813,029, filed Jun. 13, 2006.
U.S. Appl. No. 60/813,030, filed Jun. 13, 2006.
U.S. Appl. No. 60/813,075, filed Jun. 13, 2006.
U.S. Appl. No. 60/813,125, filed Jun. 13, 2006.
U.S. Appl. No. 60/813,126, filed Jun. 13, 2006.
U.S. Appl. No. 60/813,129, filed Jun. 13, 2006.
U.S. Appl. No. 60/813,131, filed Jun. 13, 2006.
U.S. Appl. No. 60/813,172, filed Jun. 13, 2006.
U.S. Appl. No. 60/813,173, filed Jun. 13, 2006.
U.S. Appl. No. 60/813,198, filed Jun. 13, 2006.
U.S. Appl. No. 60/813,207, filed Jun. 13, 2006.
U.S. Appl. No. 60/813,328, filed Jun. 13, 2006.
U.S. Appl. No. 61/334,978, filed May 14, 2010.
Cowie, Barbara M., et al., "Distributive Tactile Sensing Using Fibre Bragg Grating Sensors for Biomedical Applications," 1st IEEE / RAS-EMBS International Conference on Biomedical Robotics and Biomechatronics (BioRob 2006), Feb. 2006, pp. 312-317.
Danisch, Lee et al. "Spatially continuous six degree of freedom position and orientation sensor," Sensor Review, 1999, vol. 19, Issue 2, pp. 106-112.
Dario, Paolo et al., "A Miniature Device for Medical Intracavitary Intervention," Micro Electro Mechanical Systems '91 Proc IEEE 'An Investigation of Micro Structure, Sensors, Actuators, Machines and Robots', 1991, pp. 171-175, IEEE.
Duncan, Roger, "Sensing Shape: Fiber-Bragg-grating sensor arrays monitor shape at a high resolution," 2005, pp. 18-21, SPIE.
Extended European Search Report for Application No. EP20070798487, mailed on Jan. 30, 2015, 8 pages.
Gagarina, T. et al., "Modeling and experimental analysis of a new bellow type actuators for active catheter end-effector," Proc. 10th IEEE International Workshop on Robot and Human Interactive Communication, 2001, pp. 612-617, IEEE.
Gander, M.J. et al., "Bend measurement using Bragg gratings in multicore fibre," Electronics Letters, Jan. 20, 2000, vol. 36, No. 2, 2 Pages.
Hill, Kenneth O., "Fiber Bragg grating technology fundamentals and overview," IEEE Journal of Lightwave Technology, vol. 15, Issue 8, Aug. 1997, pp. 1263-1276.
Ikuta, Koji et al., "Development of remote microsurgery robot and new surgical procedure for deep and narrow space," Proc. IEEE International Conference on Robotics & Automation, 2003, pp. 1103-1108, vol. 1, IEEE.
Ikuta, Koji et al., "Shape memory alloy servo actuator system with electric resistance feedback and application for active endoscope," Proc. IEEE International Conference on Robotics and Automation, 1988, pp. 427-430, vol. 1, IEEE.
International Search Report for application No. PCT/US07/71085, Mailed on Sep. 17, 2008, 2 pages.
Jin, Long et al., "Two-dimensional bend sensing with a cantilever-mounted FBG [Fiber Bragg Grating]," Meas. Sci. Technol., 2006, pp. 168-172, vol. 17, Institute of Physics Publishing.
Kreger, Stephen et al., "Optical Frequency Domain Reflectometry for High Density Multiplexing of Multi-Axis Fiber Bragg Gratings," 16th International Conference on Optical Fiber Sensors (OFS-16), Oct. 2003, Nara, Japan, pp. 526-529.
Lertpiriyasuwat, Vatchara et al., "Extended Kalman Filtering Applied to a Two-Axis Robotic Arm with Flexible Links," International Journal of Robotics Research, 2000, vol. 19., No. 3, pp. 254-270.
Martinez, A. et al., "Vector Bending Sensors Based on Fibre Bragg Gratings Inscribed by Infrared Femtosecond Laser," Electronics Letters, 2005, pp. 472-474, vol. 41—Issue 8.
Measurand, "ShapeTape Overview," Measurand ShapeTape Advantage, pp. 1-3, first posted Nov. 3, 2004. Internet <www.measurand.com/products/ShapeTape_overview.html>.
Meltz, Gerald, "Overview of Fiber Grating-Based Sensors," Proceedings of SPIE Distributed Multiplexed Fiber Optic Sensors VI, Nov. 27, 1996, Eds. Kersey et al.,vol. 2838, pp. 2-22.
Office Action mailed Jun. 17, 2014 for Japanese Application No. 20130179563 filed Aug. 30, 2013, 7 pages.
Partial European Search Report for Application No. EP20120840613, mailed on Jun. 5, 2015, 5 pages.
PCT/US07/71085 Written Opinion, mailed Sep. 17, 2008, 5 pages.
PCT/US09/46446 International Search Report and Written Opinion of the International Searching Authority, mailed Dec. 14, 2009, 21 pages.
PCT/US09/46446 Partial International Search Report and Invitation to Pay Additional Fees, mailed Sep. 18, 2009, 9 pages.
PCT/US2011/035113 International Search Report and Written Opinion of the International Searching Authority, mailed Aug. 4, 2011, 13 pages.
Stieber, Michael E. et al., "Vision-Based Sensing and Control for Space Robotics Applications," IEEE Transactions on Instrumentation and Measurement, Aug. 1999, vol. 48, No. 4, pp. 807-812.
Sturges, Robert H. et al., "A Flexible, Tendon-Controlled Device for Endoscopy," The International Journal of Robotics Research, 1993, pp. 121-131, vol. 12—Issue 2, SAGE Publications.
Szewczyk, Jerome et al., "An active tubular polyarticulated microsystem for flexible endoscope," Lecture Notes in Control and Information Sciences, vol. 271, Experimental Robotics VII, 2000, pp. 179-188, Springer-Verlag.
Wang, Yi-Ping et al., "A novel long period fiber grating sensor measuring curvature and determining bend-direction simultaneously," IEEE Sensors Journal, 2005, pp. 839-843, vol. 5—Issue: 5, IEEE.
Webster, Robert J. III et al., "Toward Active Cannulas: Miniature Snake-Like Surgical Robots," 2006, 7 pages.
Wong, Allan C. L. et al., "Multiplexed fibre Fizeau interferometer and fibre Bragg grating sensor system for simultaneous measurement of quasi-static strain and temperature using discrete wavelet transform," Measurement Science and Technology, 2006, pp. 384-392, vol. 17—Issue 2, Institute of Physics Publishing.
Zhang, Lunwei et al., "FBG Sensor Devices for Spatial Shape Detection of Intelligent Colonoscope," IEEE International Conference on Robotics and Automation, Apr. 2004, New Orleans, Louisiana, pp. 835-840.

* cited by examiner

CATHETER SENSOR SYSTEMS

CROSS-REFERENCE TO RELATED APPLICATIONS

This patent document is related to and incorporates by reference the following co-filed patent applications: U.S. patent application Ser. No. 13/274,198, entitled "Catheters with Control Modes for Interchangeable Probes"; U.S. patent applicaiton Ser. No. 13/274,208, entitled "Catheters with Control Modes for Interchangeable Probes"; and U.S. patent application Ser. No. 13/274,229, entitled "Vision Probe and Catheter Systems."

BACKGROUND

Medical devices that navigate body lumens need to be physically small enough to fit within the lumens. Lung catheters, for example, which may be used to perform minimally invasive lung biopsies or other medical procedures, may need to follow airways that decrease in size as the catheter navigates branching passages. To reach a target location in a lung, a catheter may follow passages having diameters as small as 3 mm or less. Manufacturing a catheter that includes the mechanical and sensor structures suitable for remote or robotic operation and that has a diameter that is sufficiently small to navigate such small lumens can be challenging. In particular, one desirable configuration for a remotely operated catheter would provide a tool mounted on a steerable segment; tendons or pull wires that extend down the length of the catheter to an external drive system that pulls on the tendons to actuate the tool or steerable segment; lumens for suction and/or irrigation; a vision system for viewing of the target location; and sensors to identify the location of the instrument relative to the anatomy of a patient. Accommodating all of the desired features and elements of a lung catheter or other device that is robotically controlled and has a diameter about 3 mm or less can be difficult.

SUMMARY

In accordance with an aspect of the invention, a robotic catheter system using distal feedback can provide a small diameter for a distal tip of the catheter and accurate measurements of the pose of the distal tip through use of a sensor system including both electromagnetic and fiber sensors. In accordance with an aspect of the present invention, a sensor system for a catheter has a thicker proximal section containing one or more electromagnetic (EM) sensors and a thinner distal section containing a fiber shape sensor. The EM sensor can provide an accurate measurement of a base point of the distal section relative to the anatomy of a patient, while the fiber sensor measures the shape of the distal section extending from the base point. Accordingly, the distal section of the catheter can be as small as a system using only a fiber shape sensor, but the catheter system does not suffer from the inaccuracy that is common to long fiber shape sensors.

One specific embodiment of the invention is a medical system including a catheter, a first sensor system, and a second sensor system. The catheter has a first section and a second section with the second section being adjacent to the first section. The first sensor system is in the first section and configured for measurement of a pose of the first section. The second sensor system is in the second section and configured for measurement of a pose of the second section relative to the first section.

Another embodiment of the invention is a method for sensing a pose of a distal tip of an elongated flexible structure such as a catheter in a medical instrument. The method includes applying a time-varying magnetic field to a space containing at least a portion of the flexible structure. An electric signal induced in a coil positioned at a location along the flexible structure of the medical instrument can then be analyzed as part of the pose measure. The location of the coil is separated from a proximal end and the distal tip of the flexible structure. In addition to analysis of the electrical signal from the coil, a shape of a portion of the flexible structure that extends from the location of the coil toward the distal end of the flexible section is measured.

BRIEF DESCRIPTION OF THE DRAWINGS

Use of the same reference symbols in different figures indicates similar or identical items.

DETAILED DESCRIPTION

Figure 1:
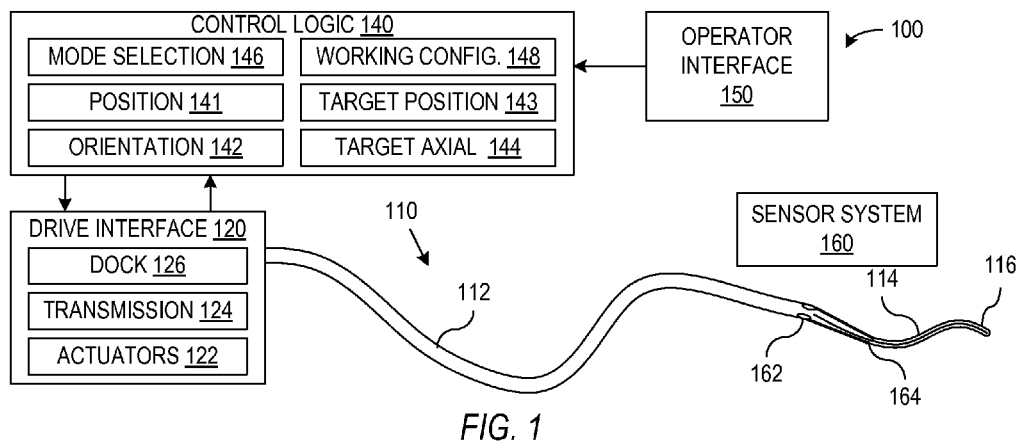
FIG. 1 shows a robotic catheter system in accordance with an embodiment of the invention having multiple control modes.

A robotic catheter for use in small lumens such as airways and passages in the respiratory tract employs combinations of one or more EM sensors and a fiber shape sensor to provide accurate measurements of the pose of a small-diameter distal tip. FIG. 1 schematically illustrates a catheter system 100 in accordance with one embodiment of the invention. In the illustrated embodiment, catheter system 100 includes a catheter 110, a drive interface 120, control logic 140, an operator interface 150, and a sensor system 160.

Figure 2:
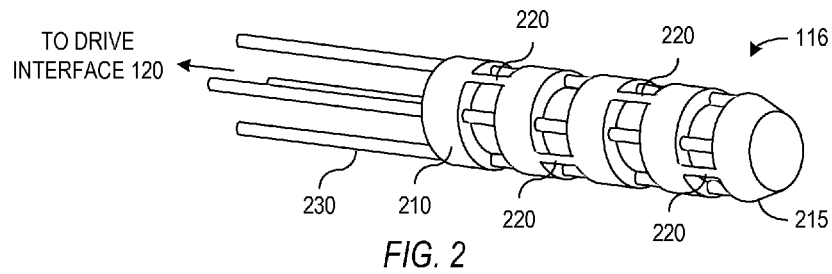
FIG. 2 shows an embodiment of a steerable segment that can be employed in the system of FIG. 1.

Catheter 110 is a generally flexible device having one or more lumens including a main lumen that can accommodate interchangeable probes such as described further below. Flexible catheters can be made using a braided structure such as a woven wire tube with inner or outer layers of a flexible or low friction material such as polytetrafluoroethylene (PTFE). In one embodiment, catheter 110 includes a bundle of lumens or tubes held together by a braided jacket and a reflowed (i.e., fused by melting) jacket of a material such as Polyether Block Amide (Pebax). Alternatively, an extrusion of a material such as Pebax can similarly be used to form multiple lumens in catheter 110. Catheter 110 particularly includes a main lumen for interchangeable probe systems and smaller lumens for pull wires and sensor lines. In the illustrated embodiment, catheter 110 has a proximal section 112 attached to drive interface 120 and a distal section 114 that extends from the proximal section 112. An additional steerable segment 116 (e.g., a metal structure such as shown in FIG. 2 and described further below) can form the distal subsection of distal section 114. Pull wires extend from drive system 120 through proximal section 112 and distal section 114 and connect to steerable segment 116.

The overall length of catheter 110 may be about 60 to 80 cm or longer with distal section 114 being about 15 cm long and steerable segment 116 being about 4 to 5 cm long. In accordance with an aspect of the invention, distal section 114 has a smaller diameter than does proximal section 112 and thus can navigate smaller natural lumens or passages. During a medical procedure, at least a portion of proximal section 112 and all of distal section 114 may be inserted along a natural lumen such as an airway of a patient. The smaller diameter of distal section 114 permits use of distal section 114 in lumens that may be too small for proximal section 112, but the larger diameter of distal section 114 facilitates inclusion of more or larger structures or devices such as electromagnetic (EM) sensors 162 that may not fit in distal section 114.

Steerable segment 116 is remotely controllable and particularly has a pitch and a yaw that can be controlled using pull wires. Steerable segment 116 may include all or part of distal section 114 and may be simply implemented as a multi-lumen tube of flexible material such as Pebax. In general, steerable segment 116 is more flexible than the remainder of catheter 110, which assists in isolating actuation or bending to steerable segment 116 when drive interface 120 pulls on actuating tendons. Catheter 110 can also employ additional features or structures such as use of Bowden cables for actuating tendons to prevent actuation from bending proximal section 112 (or bending any portion the section of 114 other than steerable segment 116) of catheter 110. FIG. 2 shows one specific embodiment in which steerable segment 116 is made from a tube 210 that in catheter 110 of FIG. 1 contains multiple tubes defining a main lumen for a probe system and smaller lumens for actuation tendons 230 and a shape sensor not shown in FIG. 2. In the illustrated embodiment, tendons 230 are placed 90° apart surrounding lumen 312 to facilitate steering catheter 110 in pitch and yaw directions defined by the locations of tendons 230. A reflowed jacket, which is not shown in FIG. 2 to better illustrate the internal structure of steerable segment 116, may also cover tube 210. As shown in FIG. 2, tube 210 is cut or formed to create a series of flexures 220. Tendons 230 connect to a distal tip 215 of steerable segment 116 and extend back to a drive interface 120. Tendons 230 can be coated or uncoated, single filament or multi strand wires, cables, Bowden cables, hypotubes, or any other structures that are able to transfer force from drive interface 120 to distal tip 215 and limit bending of proximal section 112 when drive interface 120 pulls on tendons 230. Tendons 230 can be made of any material of sufficient strength including but not limited to a metal such as steel or a polymer such as Kevlar. In operation, pulling harder on any one of tendons 230 tends to cause steerable segment 116 to bend in the direction of that tendon 230. To accommodate repeated bending, tube 210 may be made of a material such as Nitinol, which is a metal alloy that can be repeatedly bent with little or no damage.

Drive interfaces 120 of FIG. 1, which pulls on tendons 230 to actuate steerable segment 116, includes a mechanical system or transmission 124 that converts the movement of actuators 122, e.g., electric motors, into movements of (or tensions in) tendons 230 that run through catheter 110 and connect to steerable segment 116. (Push rods could conceivably be used in catheter 110 instead of tendons 230 but may not provide a desirable level of flexibility.) The movement and pose of steerable segment 116 can thus be controlled through selection of drive signals for actuators 122 in drive interface 120. In addition to manipulating tendons 230, drive interface 120 may also be able to control other movement of catheter 110 such as range of motion in an insertion direction and rotation or roll of the proximal end of catheter 110, which may also be powered through actuators 122 and transmission 124. Back-end mechanisms or transmissions that are known for flexible-shaft instruments could in general be used or modified for drive interface 120. For example, some known drive systems for flexible instruments are described in U.S. Pat. App. Pub. No. 2010/0331820, entitled "Compliant Surgical Device," which is hereby incorporated by reference in its entirety. Drive interface 120 in addition to actuating catheter 110 should allow removal and replacements of probes in catheter 110, so that the drive structure should be out of the way during such operations.

A dock 126 in drive interface 120 can provide a mechanical coupling between drive interface 120 and catheter 110 and link actuation tendons 230 to transmission 124. Dock 126 may additionally contain an electronic or optical system for receiving, converting, and/or relaying sensor signals from portions of sensor system 160 in catheter 110 and contain an electronic or mechanical system for identifying the probe or the type of probe deployed in catheter 110.

Control logic 140 controls the actuators in drive interface 120 to selectively pull on the tendons as needed to actuate and steer steerable segment 116. In general, control logic 140 operates in response to commands from a user, e.g., a surgeon or other medical personnel using operator interface 150, and in response to measurement signals from sensor system 160. However, in holding modes as described further below, control logic 140 operates in response to measurement signals from sensor system 160 to maintain or acquire a previously identified working configuration. Control logic 140 may be implemented using a general purpose computer with suitable software, firmware, and/or interface hardware to interpret signals from operator interface 150 and sensor system 160 and to generate control signals for drive interface 120.

In the illustrated embodiment, control logic 140 includes multiple modules 141, 142, 143, and 144 that implement different processes for controlling the actuation of catheter 110. In particular, modules 141, 142, 143, and 144 respectively implement a position stiffening mode, an orientation stiffening mode, a target position mode, and a target axial mode, which are described further below. A module 146 selects which control process will be used and may base the selection on user input, the type or status of the probe deployed in catheter 110, and the task being performed. Control logic 140 also includes memory storing parameters 148 of a working configuration of steerable segment 116 that is desired for a task, and each of the modules 141, 142, 143, and 144 can use their different control processes to actively maintain or hold the desired working configuration.

Operator interface 150 may include standard input/output hardware such as a display, a keyboard, a mouse, a joystick, or other pointing device or similar I/O hardware that may be customized or optimized for a surgical environment. In general, operator interface 150 provides information to the user and receives instructions from the user. For example, operator interface 150 may indicate the status of system 100 and provide the user with data including images and measurements made by system 100. One type of instruction that the user may provide through operator interface 150, e.g., using a joystick or similar controller, indicates the desired movement or position of steerable segment 116, and using such input, control logic 140 can generate control signals for actuators in drive interface 120. Other instructions from the user can, for example, select an operating mode of control logic 140.

Sensor system 160 generally measures a pose of steerable segment 116. In the illustrated embodiment, sensor system 160 includes EM sensors 162 and a shape sensor 164. EM sensors 162 include one or more conductive coils that may be subjected to an externally generated electromagnetic field. Each coil of EM sensors 162 then produces an induced electrical signal having characteristics that depend on the position and orientation of the coil relative to the externally generated electromagnetic field. In an exemplary embodiment, EM sensors 162 are configured and positioned to measure six degrees of freedom, e.g., three position coordinates X, Y, and Z and three orientation angles indicating pitch, yaw, and roll of a base point. The base point in system 100 is at or near the end of proximal section 112 and the start of distal section 114 of catheter 110. Shape sensor 164 in the exemplary embodiment of the invention includes a fiber grating that permits determination of the shape of a portion of catheter 110 extending from the base point, e.g., the shape of distal section 114 or steerable segment 116. Such shape sensors using fiber gratings are further described in U.S. Pat. No. 7,720,322, entitled "Fiber Optic Shape Sensor," which is hereby incorporated by reference in its entirety. An advantage of the illustrated type of sensor system 160 is that EM sensors 162 can provide measurements relative to the externally generated magnetic field, which can be calibrated relative to a patient's body. Thus, system 160 can use EM sensors 162 to reliably measure the position and orientation of a base point for shape sensor 164, and shape sensor 164 need only provide shape measurement for a relatively short distance. Additionally, distal section 114 only contains shape sensor 164 and may have a diameter that is smaller than the diameter of proximal section 112. More generally, sensor system 160 need only be able to measure the pose of steerable segment 116, and other types of sensors could be employed.

Figures 3A, 3B:
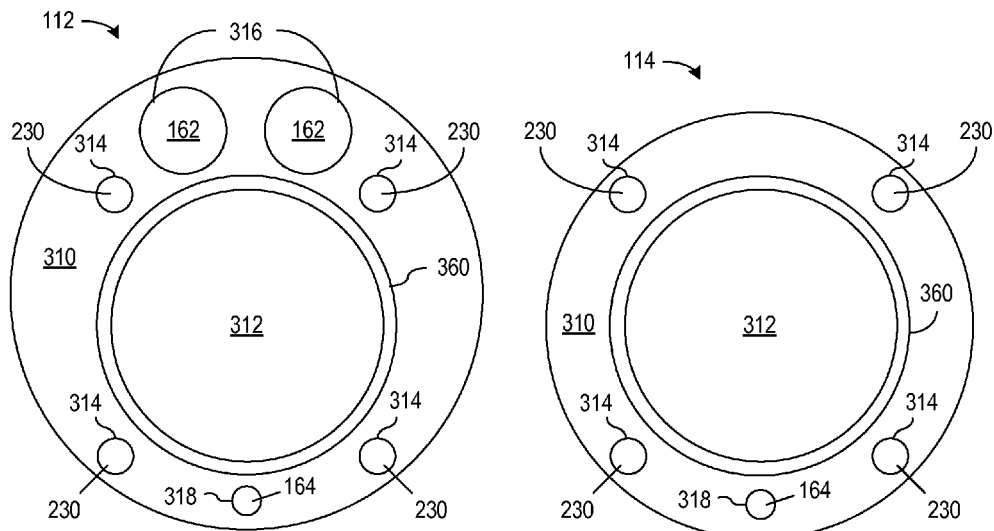
FIGS. 3A and 3B show cross-sectional views of proximal and distal sections of a catheter in accordance with an embodiment of the invention.

FIGS. 3A and 3B respectively show cross-sections of the proximal and distal sections 112 and 114 of catheter 110 in one embodiment of the invention. FIG. 3A shows an embodiment of catheter 110 having a body 310 that includes a main lumen 312 for a vision or medical probe, lumens 314 containing tendons 230, lumens 316 containing EM sensors 162 or associated signal wires, and a lumen 318 containing a fiber shape sensor 164. Main lumen 312, tendon lumens 314, and a shape sensor lumen 318 extend into distal section 114 as shown in FIG. 3B, but lumens 316 for EM sensors 162 are not needed in distal section 114 because EM sensors 162 are only in proximal section 112. Accordingly, distal section 114 can be smaller than proximal section 112 particularly because the lumen 318 for fiber shape sensor 164 fits between two lumens 314 for pull wires and does not negatively affect the outside diameter of distal section 114. In an exemplary embodiment, body 310 in proximal section 112 has an outer diameter of about 4 mm (e.g., in a range from 3 to 6 mm) and provides main lumen 312 with a diameter of about 2 mm (e.g., in a range from 1 to 3 mm) and in distal section 114 has an outer diameter of about 3 mm (e.g., in a range from 2 to 4 mm) while maintaining the diameter of main lumen 312 at about 2 mm. A smooth taper (as shown in FIG. 1) or an abrupt step in body 310 can be used at the transition from the larger diameter of proximal section 112 to the smaller diameter of distal section 114.

The specific dimensions described in above are primarily for a catheter that accommodates probes having a diameter of 2 mm, which is a standard size for existing medical tools such as lung biopsy probes. However, alternative embodiments of the invention could be made larger or smaller to accommodate medical probes with a larger or smaller diameter, e.g., 1 mm diameter probes. A particular advantage of such embodiments is that a high level of functionality is provided in a catheter with relative small outer diameter when compared to the size of probe used in the catheter.

FIGS. 3A and 3B also show a sheath 360 that may be employed between catheter body 310 and a probe in main lumen 312. In one embodiment of catheter 110, sheath 360 is movable relative to body 310 and can be extended beyond the end of steerable segment 116. This may be advantageous in some medical procedures because sheath 360 is even smaller than distal section 114 and therefore may fit into smaller natural lumens or passages. For example, if catheter 110 reaches a branching of lumens that are too small to accommodate steerable segment 116, steerable segment 116 may be pointed in the direction of the desired branch, so that sheath 360 can be pushed beyond the end of steerable segment 116 and into that branch. Sheath 360 could thus reliably guide a medical probe into the desired branch. However, sheath 360 is passive in that it is not directly actuated or steerable. In contrast, distal section 114 accommodates actuation tendons 230 that connect to steerable segment 116 and can be manipulated to steer or pose steerable segment 116. In some medical applications, the active control of steerable segment 116 is desirable or necessary during a medical procedure, and passive sheath 360 may not be used in some embodiments of the invention.

Figure 4:
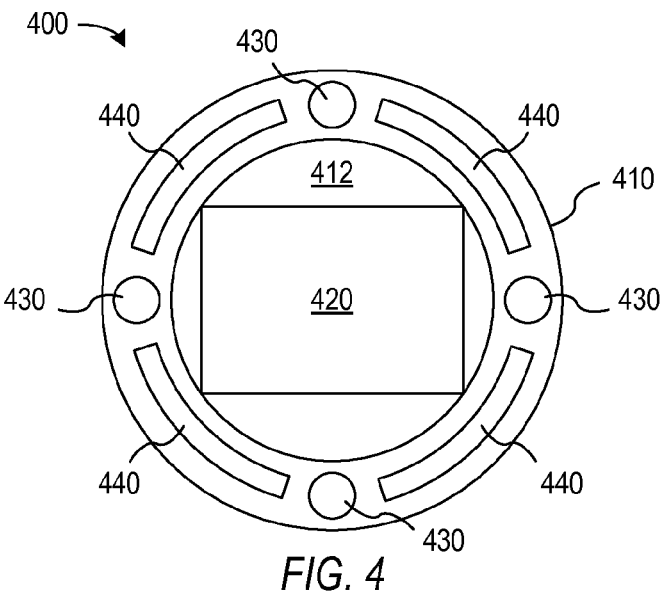
FIG. 4 shows a cross-sectional view of a vision probe that may be deployed in the catheter of FIGS. 3A and 3B and swapped out for use of medical probes in the catheter shown in FIGS. 3A and 3B.

Main lumen 312 is sized to accommodate a variety of medical probes. One specific probe is a vision probe 400 such as illustrated in FIG. 4. Vision probe 400 has a flexible body 410 with an outer diameter (e.g., about 2 mm) that fits within the main lumen of catheter 110 and with multiple inner lumens that contain the structures of vision probe 400. Body 410 may be formed using an extruded flexible material such as Pebax or another polymer, which allows creation of multiple lumens and thin walls for maximal utility in minimal cross-sectional area. A multi-lumen extrusion also neatly organizes the location of the components. The length of body 410 may optionally include a combination of two multi-lumen extrusions, for example, a distal extrusion "butt-welded" to a proximal extrusion. This may be done, for example, so that the proximal or distal extrusion has desired shape, e.g., a clover-leaf or oval outside shape, to mate with a complementary keying feature in catheter 110. These mating shapes or keying structures can prevent the probe from rotating within the catheter and assure a known orientation of camera 320 relative to catheter 110.

In the illustrated embodiment, the structure of vision probe 400 includes a CMOS camera 420, which is at the distal end of the probe and connected through one or more signal wires (not shown) that extend along the length of vision probe 400, e.g., to provide a video signal to control logic 140 or operator interface 150 as shown in FIG. 1. Alternatively, a fiber bundle imaging system could be employed, but CMOS cameras 420 can typically provide images of higher quality than can be achieved with fiber bundle imaging systems. Vision probe 400 also includes illumination fibers 430 that surround camera 420 and provide light for imaging within a body lumen. In an exemplary embodiment, illumination fibers 430 are made of a flexible material such as plastic, which tends to be more flexible than glass fibers. Oblong fluid ports 440 are provided in body 410 for suction and irrigation that may be useful, for example, for rinsing of a lens of camera 420. Fluid ports 440 can also be used for delivering drugs, e.g., for numbing, before vision probe 400 is removed from catheter 110 and replaced with a biopsy probe. Although the illustrated embodiment of vision probe 400 includes multiple fluid ports 440, a single fluid port could be used for both irrigation and suction, and vision probe 400 could alternatively have only a single fluid port to save space. Vision probe 400 may additionally include an electromagnetic sensor (not shown) embedded just proximally to CMOS camera 420 to provide additional pose information about the tip of vision probe 400.

Vision probe 400 is adapted to be inserted or removed from catheter 110 while catheter 110 is in use for a medical procedure. Accordingly, vision probe 400 is generally free to move relative to catheter 110. While movement relative to catheter 110 is necessary or desirable during insertion or removal of vision probe 400, the orientation of a vision probe 400 (and some medical probes) may need to be known for optimal or easier use. For example, a user viewing video from vision probe 400 and operating a controller similar to a joystick to steer catheter 110 generally expects the directions of movement of the controller to correspond to the response of steerable segment 116 and the resulting change in the image from vision probe 400. Operator interface 150 needs (or at least can use) information on the orientation of vision probe 400 relative to tendons 230 in order to provide a consistency in directions used in the user interface. In accordance with an aspect of the invention, a keying system (not shown) can fix vision probe 400 into a known orientation relative to catheter 110 and tendons 230. The keying system may, for example, be implemented through the shape of a proximal or distal section of probe 400 or include a spring, fixed protrusion, or latch on vision probe 400 or steerable segment 116 and a complementary notch or feature in steerable segment 116 or vision probe 400.

Vision probe 400 is only one example of a probe system that may be deployed in catheter 110 or guided through catheter 110 to a work site. Other probe systems that may be used include, but are not limited to, biopsy forceps, biopsy needles, biopsy brushes, ablation lasers, and radial ultrasound probes. In general, catheter 110 can be used with existing manual medical probes that are commercially available from medical companies such as Olympus Europa Holding GmbH.

Figure 5:
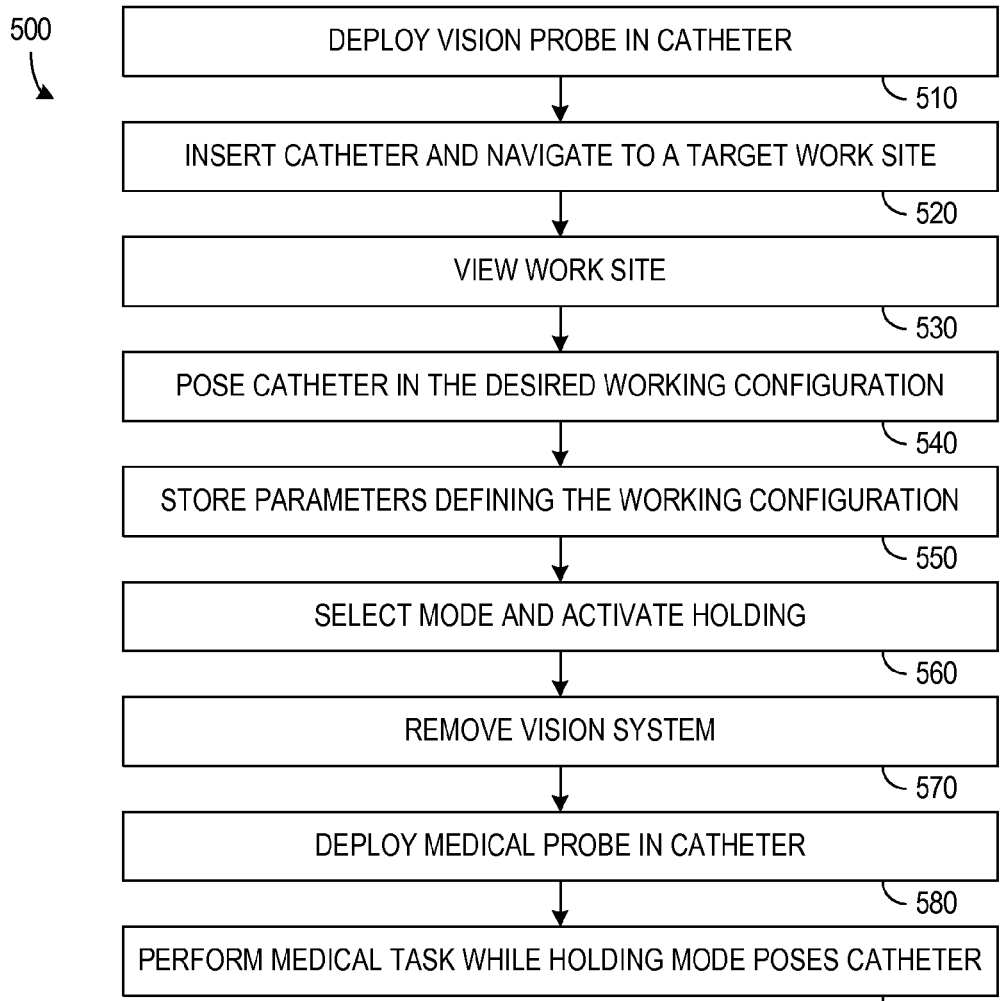
FIG. 5 is a flow diagram of a process for using the catheter system with a removable vision system and multiple control modes.

The catheter system 100 of FIG. 1 can be used in procedures that swap a vision probe and a medical probe. FIG. 5 is a flow diagram of one embodiment of a process 500 for using the catheter system 100 of FIG. 1. In process 500, vision probe 400 is deployed in catheter 110 in step 510, and catheter 110 is inserted along a path including a natural lumen of a patient. For example, for a lung biopsy, steerable segment 116 of catheter 110 may be introduced through the mouth of a patient into the respiratory tract of the patient. Vision probe 400 when fully deployed in catheter 110 may fit into a keying structure that keeps vision probe 400 in a desired orientation at or even extending beyond steerable segment 116 to provide a good forward view from steerable segment 116 of catheter 110. As noted above, steerable segment 116 of catheter 110 is steerable, and vision probe 320 can provide video of the respiratory tract that helps a user when navigating catheter 110 toward a target work site. However, use of vision probe 400 during navigation is not strictly necessary since navigation of catheter 110 may be possible using measurements of sensor system 160 or some other system with or without vision probe 400 being deployed or used in catheter 110. The path followed to the work site may be entirely within natural lumens such as the airways of the respiratory track or may pierce and pass through tissue at one or more points.

When steerable segment 116 reaches the target work site, vision probe 400 can be used to view the work site as in step 530 and to pose steerable segment 116 for performance of a task at the target work site as in step 540. Posing of steerable segment 116 may use images or visual information from vision probe 400 and measurements from sensor system 160 to characterize the work site and determine the desired working configuration. The desired working configuration may also depend on the type of tool that will be used or the next medical task. For example, reaching a desired working configuration of catheter 110 may bring the distal tip of steerable segment 116 into contact with tissue to be treated, sampled, or removed with a medical tool that replaces vision probe 400 in catheter 110. Another type of working configuration may point steerable segment 116 at target tissue to be removed using an ablation laser. For example, tissue could be targeted in one or more 2D camera views while vision probe 400 is still in place in catheter 110, or target tissue can be located on a virtual view of the work site using pre-operative 3D imaging data together with the position sensing relative to patient anatomy. Still another type of working configuration may define a line for the insertion of a needle or other medical tool into tissue, and the working configuration includes poses in which the distal tip of steerable segment 116 is along the target line. In general, the desired working configuration defines constraints on the position or the orientation of the distal tip of steerable segment 116, and the shape of more proximal sections of catheter 110 is not similarly constrained and may vary as necessary to accommodate the patient.

Step 550 stores in memory of the control logic parameters that identify the desired working configuration. For example, the position of a distal tip or target tissue can be defined using three coordinates. A target line for a need can be defined using the coordinates of a point on the line and angles indicating the direction of the line from that point. In general, control logic 120 uses the stored parameters that define the desired working configuration when operating in a holding mode that maintains steerable segment 116 of catheter 110 in the desired working configuration as described further below.

Step 560 selects and activates a holding mode of the catheter system after the desired working configuration has been established and recorded. Control logic 140 for catheter 110 of FIG. 1 may have one or more modules 141, 142, 143, and 144 implementing multiple stiffening modes that may be used as holding modes when the desired configuration of steerable segment 116 has fixed constraints. The available control modes may include one or more of the following.

1.) A position stiffness mode compares the position of the distal tip of steerable segment 116 as measured by sensor system 160 to a desired tip position and controls the actuators to minimize the difference in desired and measured tip positions. The position stiffness mode may particularly be suitable for general manipulation tasks in which the user tries to precisely control the position of the tip and for situations where the distal tip contacts tissue.

2.) An orientation stiffness mode compares the measured orientation or pointing direction of the distal tip to a desired pointing direction of the distal tip and controls the actuators to minimize the difference in desired and actual tip pointing direction. This orientation stiffening that may be suitable, e.g., when controlling an imaging device such as vision probe 400 attached steerable segment 116, in which case the viewing direction is kept as desired, while the exact position of steerable segment 116 may be less important.

3.) A target position stiffness mode uses a combination of the measured tip position and pointing direction to control catheter 110 to always point the distal tip of steerable segment 116 towards a specified target point some distance in front of steerable segment 116. In case of external disturbances, control logic 140 may control the actuators to implement this target position stiffening behavior, which may be suitable, e.g., when a medical probe inserted though the catheter contains an ablation laser that should always be aimed at a target ablation point in tissue.

4.) A target axial motion stiffness mode uses a combination of the measured tip position and pointing direction to ensure that the distal tip of steerable segment 116 is always on a line in space and has a pointing direction that is also along that line. This mode can be useful, e.g., when inserting a biopsy needle along a specified line into tissue. Tissue reaction forces could cause the flexible section of catheter 110 to bend while inserting the needle, but this control strategy would ensure that the needle is always along the right line.

The selection of a mode in step 560 could be made through manual selection by the user, based on the type of probe that is being used (e.g., grasper, camera, laser, or needle) in catheter 110, or based on the activity catheter 110 is performing. For example, when a laser is deployed in catheter 110, control logic 120 may operate in position stiffness mode when the laser deployed in catheter 110 is off and operate in target position stiffness mode to focus the laser on a desired target when the laser is on. When "holding" is activated, control logic 140 uses the stored parameters of the working configuration (instead of immediate input from operator interface 150) in generating control signals for drive interface 120.

The vision probe is removed from the catheter in step 570, which clears the main lumen of catheter 110 for the step 580 of inserting a medical probe or tool through catheter 110. For the specific step order shown in FIG. 5, control logic 140 operates in holding mode and maintains steerable segment 116 in the desired working configuration while the vision system is removed (step 570) and the medical probe is inserted (step 580). Accordingly, when the medical probe is fully deployed, e.g., reaches the end of steerable segment 116, the medical probe will be in the desired working configuration, and performance of the medical task as in step 590 can be then performed without further need or use of the removed vision probe. Once the medical task is completed, the catheter can be taken out of holding mode or otherwise relaxed so that the medical probe can be removed. The catheter can then be removed from the patient if the medical procedure is complete, or the vision or another probe can be inserted through the catheter if further medical tasks are desired.

In one alternative for the step order of process 500, catheter 110 may not be in a holding mode while the medical probe is inserted but can be switched to holding mode after the medical probe is fully deployed. For example, catheter 110 may be relaxed or straightened for easy remove of vision probe 400 (step 570) and insertion of the medical probe (step 580). Once holding mode is initiated, e.g., after insertion of the medical probe, control logic 140 will control the drive interface 130 to return steerable segment 116 to the desired working configuration if steerable segment 116 has moved since being posed in the desired working configuration. Thereafter, control logic 140 monitors the pose of steerable segment 116 and actively maintains steerable segment 116 in the desired working configuration while the medical task is performed in step 590.

Figure 6:
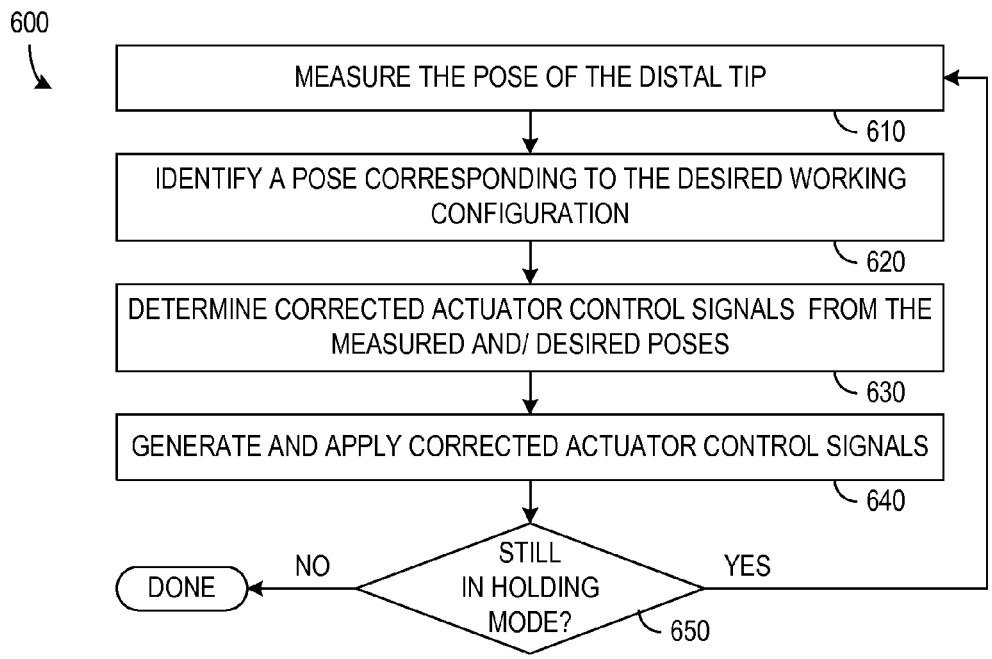
FIG. 6 is a flow diagram of a catheter control process in a holding mode.

FIG. 6 shows a flow diagram of a process 600 of a holding mode that can be implemented in control logic 140 of FIG. 1. Process 600 begins in step 610 with receipt of measurement signals from sensor system 160. The particular measurements required depend on the type of holding mode being implemented, but as an example, the measurements can indicate position coordinates, e.g., rectangular coordinates X, Y, and Z, of the distal tip of steerable segment 116 and orientation angles, e.g., angles $\theta_X$, $\theta_Y$, and $\theta_Z$ of a center axis of the distal tip of steerable segment 116 relative to coordinate axes X, Y, and Z. Other coordinate systems and methods for representing the pose of steerable segment 116 could be used, and measurements of all coordinates and direction angles may not be necessary. However, in an exemplary embodiment, sensor system 160 is capable of measuring six degrees of freedom (DoF) of the distal tip of steerable segment 116 and of providing those measurements to control logic 140 in step 610.

Control logic 140 in step 620 determines a desired pose of steerable segment 116. For example, control logic 140 can determine desired position coordinates, e.g., X', Y', and Z', of the end of steerable segment 116 and desired orientation angles, e.g., angles $\theta'_X$, $\theta'_Y$, and $\theta'_Z$ of the center axis of steerable segment 116 relative to coordinate axes X, Y, and Z. The holding modes described above generally provide fewer than six constraints on the desired coordinates. For example, position stiffness operates to constrain three degrees of freedom, the position of the end of steerable segment 116 but not the orientation angles. In contrast, orientation stiffness mode constrains one or more orientation angles but not the position of end of steerable segment 116. Target position stiffness mode constrains four degrees of freedom, and axial stiffness mode constrains five degrees of freedom. Control logic 610 can impose further constraints to select one of set of parameters, e.g., X', Y', and Z' and angles $\theta'_X$, $\theta'_Y$, and $\theta'_Z$, that provides the desired working configuration. Such further constraints include but are not limited to mechanical constraints required by the capabilities of steerable segment 116 and of catheter 110 generally and utilitarian constraints such as minimizing movement of steerable segment 116 or providing desired operating characteristics such as smooth, non-oscillating, and predictable movement with controlled stress in catheter 110. Step 620 possibly includes just keeping a set pose steerable segment 116 by finding smallest movement from the measured pose to a pose satisfying the constraints, e.g., finding the point on the target line closest to the measure position for axial motion stiffness or finding some suitable pose from registered pre-op data that is close to the current pose.

Control logic 140 in step 630 uses the desired and/or measured poses to determine corrected control signals that will cause drive interface 120 to move steerable segment 116 to the desired pose. For example, the mechanics of catheter 110 and drive interface 120 may permit development of mappings from the desired coordinates X', Y', and Z' and angles $\theta'_X$, $\theta'_Y$, and $\theta'_Z$ to actuator control signals that provide the desired pose. Other embodiments may use differences between the measured and desired pose to determine corrected control signals. In general, the control signals may be used not only to control actuators connected through tendons to steerable segment 116 but may also control (to some degree) insertion or roll of catheter 110 as a whole.

A branch step 650 completes a feedback loop by causing process 600 to return to measurement step 610 after control system 140 applies new control signals drive interface 120. The pose of distal tip is thus actively monitored and controlled according to fixed constraints as long as control system 120 remains in the holding mode. It may be noted, however, that some degrees of freedom of steerable segment 116 may not require active control. For example, in orientation stiffness mode, feedback control could actively maintain pitch and yaw of steerable segment 116, while the mechanical torsional stiffness of catheter 110 is relied on hold the roll angle fixed. However, catheter 110 in general may be subject to unpredictable external forces or patient movement that would otherwise cause catheter 110 to move relative to the work site, and active control as in process 600 is needed to maintain or hold the desired working configuration.

The sensor system 160 of a catheter 100 as noted above can employ both an EM sensor 162 and a fiber shape sensor 164. EM sensors or trackers are state-of-the-art position and orientation sensors that combine high global accuracy with small package size (e.g., about 1×10 mm). EM sensors are commercially available from companies such as Ascension Technology Corporation and Northern Digital Inc. Shape sensing technology, which may be used in the above described embodiments, commonly employ reflections and interference within an optical fiber to measure the shape along the length of the optical fiber. This shape sensing technology is good for giving 6-DoF relative measurements between two points along the fiber as well as measuring bend angles of controllable joints or providing full three-dimensional shape information. A typical fiber shape sensor of this type may have a diameter of about 0.2 mm, which is considerably smaller than a typical EM sensor.

Figure 7:
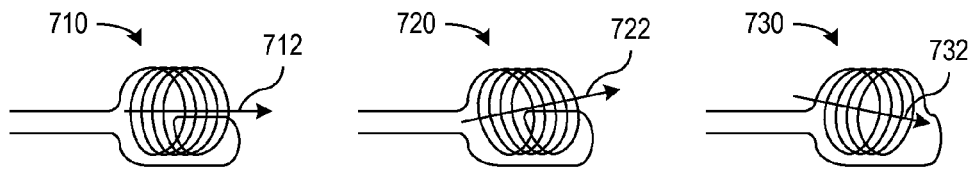
FIG. 7 shows sensing coils that can be employed in electromagnetic sensors in medical systems in some embodiments of the invention.

FIG. 7 illustrates three different types of sensing coils 710, 720, and 730 that could be used in an EM sensor. In operation, the sensing coil, e.g., coil 710, in the catheter or other device is placed in a well-controlled magnetic field that an external EM generator produces. The EM generator typically has the form of a square or cylindrical box of 20-60 cm wide and several cm thick and may have a fixed position relative to the patient. The magnetic field produced by the generator varies in time and induces a voltage and electric current in the sensing coil 710. U.S. Pat. No. 7,197,354, entitled "System for Determining the Position and Orientation of a Catheter"; U.S. Pat. No. 6,833,814, entitled "Intrabody Navigation System for Medical Applications"; and U.S. Pat. No. 6,188,355, entitled "Wireless Six-Degree-of-Freedom Locator" describe the operation of some EM sensor systems suitable for in medical environment and are hereby incorporated by reference in their entirety. U.S. Pat. No. 7,398,116, entitled "Methods, Apparatuses, and Systems useful in Conducting Image Guided Interventions," U.S. Pat. No. 7,920,909, entitled "Apparatus and Method for Automatic Image Guided Accuracy Verification," U.S. Pat. No. 7,853,307, entitled "Methods, Apparatuses, and Systems Useful in Conducting Image Guided Interventions," and U.S. Pat. No. 7,962,193, entitled "Apparatus and Method for Image Guided Accuracy Verification" further describe systems and methods that can use electromagnetic sensing coils in guiding medical procedures and are also incorporated by reference in their entirety. In general, the induced voltage in a sensing coil depends on time derivative the magnetic flux, which in turn depends on the strength of the magnetic field and the direction of the magnetic field relative to a normal to the areas of loops in the coil. The field generator can vary the direction and magnitude of the magnetic field in a systematic manner that enables at least partial determination of the pose of coil 710 from the induced electric signal. Up to five degrees of freedom can be determined using a sensor 162 containing a single sensing coil 710. However, sensing coil 710 is cylindrically symmetric, so that a roll angle, i.e., an angle indicating orientation about a normal 712 to the inductive areas of coil 710, cannot be determined. Only the position and the pointing direction can be determined using a single coil 710. Even so, a 5-Degree-of-Freedom (5-DoF) sensor containing a single sensing coil 710 is useful in many medical systems. In particular, the mechanical shape of a typical sensing coil (long and slender) fits well with the mechanical shape of minimally invasive medical tools, and if the tool is rotationally symmetrical (e.g. in the case of a needle or laser fiber), the roll angle is not relevant.

A robotic control catheter such as catheter 110 may need a 6-DoF measurement including a measurement of the roll angle so that the positions of actuating tendons are known. If measurement of the roll angle is of interest, two 5-DoF EM sensors can be combined to create a 6-DoF EM sensor. One specific configuration of a 6-DoF EM sensor uses two coils such as 710 with the inductive areas of two coils having normal vectors that are askew, e.g., perpendicular to each other. More generally, the two coils need to be arranged so that the normal vectors to inductive areas are not along the same axis, and larger angles between the normal vectors generally provide better measurement accuracy. Coils 720 and 730 illustrate how a coil 720 or 730 that may have wire loops with a normal 722 or 732 that is at a non-zero angle to the axes of a cylinder containing the coil 720 or 730. Coils 720 and 730 can thus be oriented along the same direction, e.g., along the length of a catheter or other medical tool, and still be used to measure six degrees of freedom.

Figure 8A:
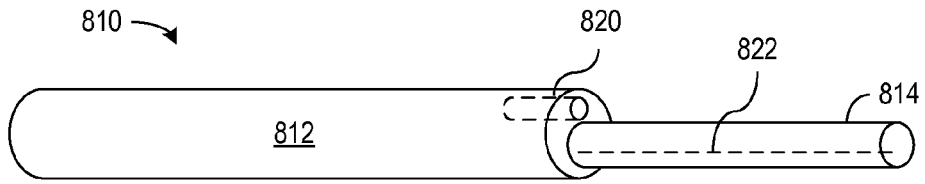
FIGS. 8A, 8B, 8C, and 8D illustrate alternative configurations for sensor systems in accordance with embodiments of the invention including electromagnetic and shape sensors.

FIG. 8A shows a configuration of a catheter system 810 having a proximal section 812 containing a 6-DoF EM sensor 820 and a distal section 814 containing a fiber shape sensor 822. EM sensor 820 terminates at or near a distal end of proximal section 812. Accordingly, distal section 814 can have a diameter (e.g., about 3 mm to accommodate a probe diameter of about 2 mm) that is smaller than the diameter (e.g., about 4 mm) of proximal section 812 because EM sensor 820 does not extend into distal section 814. The pose of distal tip of section 814 can be determined using EM sensor 820 to measure or determine the global position and orientation of a point along shape sensor 822 and using shape sensor 822 to determine the shape of distal section 814 extending from the measured point. The accuracy of shape sensor 822 can be relatively high because shape sensor 822 only needs to measure the shape of a relatively short section 814 of catheter 810, rather than the entire length of catheter 810. For example, in one case, the accuracy of the position measurement for the distal tip of section 814 is a function of the position and orientation accuracy of the EM sensor 820 (typically about 1 mm and 0.01 radians respectively) and the position accuracy of the shape sensor (0.15% of the length of section 814). If 6-DoF EM sensor 820 is about 115 mm away from the distal tip, the typical tip position accuracy would be about 2.5 mm.

Figure 8B:
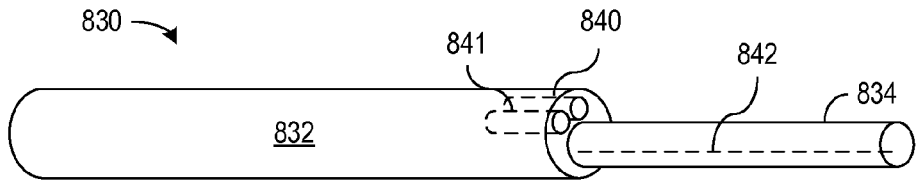
Figure 9:
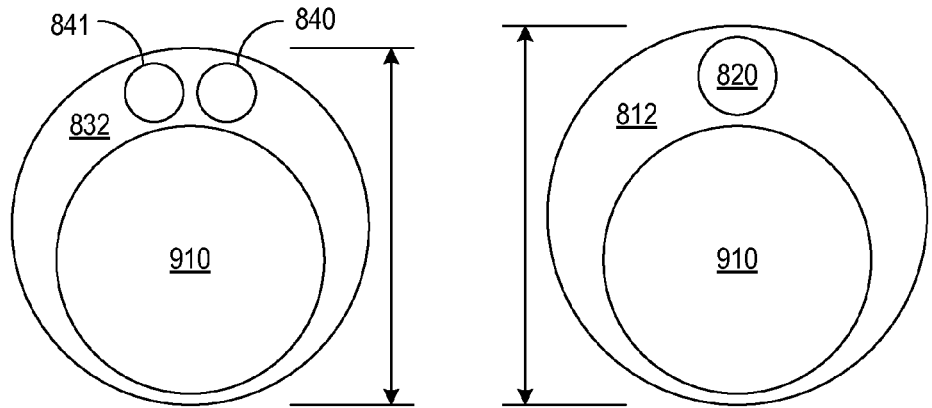
FIG. 9 shows cross-sections of a catheter system containing a six-degree-of-freedom EM sensor and a catheter system containing two five-degree-of-freedom EM sensors.

FIG. 8B shows a catheter 830 that uses two 5-DoF EM sensors 840 and 841 in a proximal section 832 to measure six degrees of freedom of a base point along a shape sensor 842 that extends into a distal section 834 of catheter 830. Coils of EM sensors 840 and 841 are within the same cross-section of proximal section 832 and therefore are rigidly fixed relative to each other. EM sensors 840 and 841 can also contain sensing coils such as coils 720 and 730 having wire loops with different orientations to measure different degrees of freedom of a point along shape sensor 842. The roll angle can thus be determined using the two measured pointing directions of sensors 840 and 841 to define a reference frame. The use of 5-DoF sensors 840 and 841 may allow a reduction in the diameter of proximal section 832. In particular, 6-DoF EM sensors that are available commercially generally have diameters that are larger than the diameters of similar 5-DoF EM sensors. In accordance with an aspect of the current invention, the diameter of a catheter may be decreased through use of 5-DoF EM sensors. FIG. 9, for example, illustrates how a distal section 832 of catheter 830 can accommodate two 5-DoF EM sensors 840 and 841 and a main lumen 910 within a circular cross-sectional area that is smaller than the area of distal section 812 of catheter 810. In particular, section 812 is larger because section 812 must accommodate the main lumen and a 6-DoF sensor that has a larger diameter than do 5-DoF sensors 840 and 841.

Figure 8C:
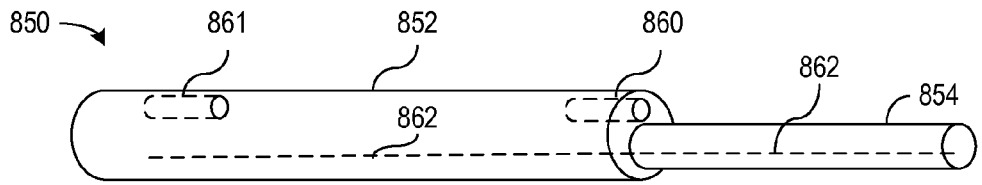

FIG. 8C shows an embodiment of the invention using a sensor system that may allow a proximal section 852 of catheter 850 to be even smaller by using two 5-DoF EM sensors 860 and 861 that are separated along the length of the proximal section 852. Accordingly, only one 5-DoF EM sensor 860 or 861 needs to be accommodated within the cross-section of proximal section 852. However, since distal section 852 is flexible and may be bent when in use, EM sensors 860 and 861 are not rigidly fixed relative to each other, and a shape sensor 862 is used to measure the shape of the portion of proximal section 852 between EM sensors 861 and 860 and the relative orientation of EM sensors 860 and 861. The shape measurement between EM sensors 861 and 860 indicates the position and orientation of sensor 860 relative to sensor 861, and the relative configuration is needed for determination of a 6-DoF measurement from the two 5-DoF measurement. Shape sensor 862 also measures the shape of distal section 854, which indicates the position and orientation of the distal tip relative to the global position and orientation measurements determined using EM sensors 860 and 861.

Figure 8D:
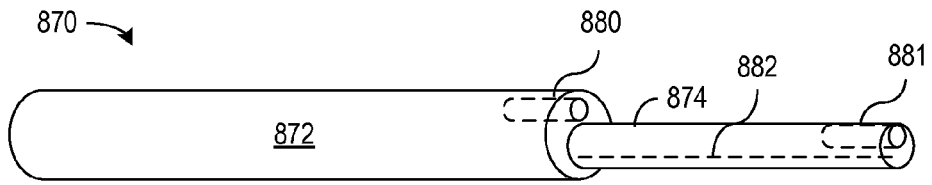

FIG. 8D shows yet another catheter 870 using two 5-DoF EM sensors 880 and 881 that are separate along the length of catheter 870. The sensing system in catheter 870 of FIG. 8D differs from the sensing systems of FIGS. 8A, 8B, and 8C in that one EM sensor 880 is located in a proximal section 872 of catheter 870 and the other EM sensor 881 is located in a distal section 874 of catheter 870. Accordingly, distal section 874 must be large enough to include sensor 881, but still may allow a reduction in the diameter of catheter 870 when compared to a catheter having a 6-DoF EM sensor at a distal tip.

The use of two 5-DoF EM sensors in embodiments of FIGS. 8B, 8C, and 8D provides more information than is strictly required for a 6-DoF measurement. In accordance with a further aspect of the invention, one of the two 5-DoF EM sensors in catheter 830, 850, or 870 of FIG. 8B, 8C, or 8D could be replaced with another type of sensor that may not measure five degrees of freedom. For example, an accelerometer could be employed in place of one of the two EM sensors and provide a measurement of the direction of gravity, i.e., down. Provided that the symmetry axis of the 5-DoF sensor is not vertical, the combination of the measurements of a 5-DoF sensor and a measurement of the orientation relative to the vertical direction is sufficient to indicate measurements for six degrees of freedom.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A medical system comprising:
a catheter having a first section and a second section, the second section adjacent to the first section, wherein the first section defines a first longitudinal catheter axis and the second section defines a second longitudinal catheter axis;
an electromagnetic sensor system in the first section including:
a first electromagnetic sensor in a first lumen portion extending along a longitudinal sensor axis in parallel with the first longitudinal catheter axis at a proximal end of the first section, and
a second electromagnetic sensor in a second lumen portion extending along the longitudinal sensor axis in parallel with the first longitudinal catheter axis at a distal end of the first section, the distal end of the first section being adjacent to the second section,
wherein the first section between the proximal and distal ends flexibly couples the first and second electromagnetic sensors so that the first electromagnetic sensor is movable with respect to the second electromagnetic sensor, wherein the first electromagnetic sensor includes a first signal wire coupled to a first coil extending within the first lumen portion along the longitudinal sensor axis and the second electromagnetic sensor includes a second signal wire coupled to a second coil extending within the second lumen portion along the longitudinal sensor axis; and
a fiber shape sensor system that extends through the first section between and along the first electromagnetic sensor and the second electromagnetic sensor, the fiber shape sensor extending through the second section, the fiber shape sensor system being configured for measurement of a pose of the second section relative to the distal end of the first section and measurement of a relative orientation between the first electromagnetic sensor and the second electromagnetic sensor.

2. The system of claim 1, wherein the second section is narrower than the first section.

3. The system of claim 2, wherein the first longitudinal catheter axis is offset from the second longitudinal catheter axis.

4. The system of claim 1, wherein the first electromagnetic sensor is configured to measure a position and an orientation of the proximal end of the first section relative to an external reference.

5. The system of claim 4, wherein the second electromagnetic sensor is configured to measure a position and an orientation of the distal end of the first section relative to the proximal end of the first section.

6. The system of claim 1, wherein the first electromagnetic sensor and the second electromagnetic sensor are five-degree-of-freedom sensors and wherein the electromagnetic sensor system and the fiber shape sensor system comprise a measurement system for determining a six-degree-of-freedom measurement.

7. The system of claim 1, wherein the fiber shape sensor system comprises Bragg gratings.

8. The system of claim 1, wherein
the first coil has a first magnetic axis oriented at a first angle relative to the first longitudinal catheter axis; and
the second coil has a second magnetic axis that is oriented at a second angle relative to the first longitudinal catheter axis, the first and second angles being different such that the second magnetic axis is askew from the first magnetic axis.

9. The system of claim 1, wherein the fiber shape sensor system is configured to measure a spatial relationship between the first coil and the second coil.

10. The system of claim 1, wherein the first section further comprises an accelerometer configured to measure a direction of gravity.

11. A method for sensing a pose of a distal tip of an elongated flexible structure of a medical instrument, the method comprising:
applying a time-varying magnetic field to a space containing at least a portion of the elongated flexible structure, the elongated flexible structure defining an instrument longitudinal axis and comprising a catheter;

analyzing an electric signal induced in a first coil positioned with a first signal wire in a first lumen portion having a sensor longitudinal axis arranged in parallel with the instrument longitudinal axis at a first location along the flexible structure of the medical instrument, wherein the first location is separated from a proximal end and a distal end of the flexible structure; and measuring, with a shape sensor, a shape of a portion of the flexible structure of the medical instrument, wherein the portion measured extends from the first location of the first coil toward the distal end of the flexible structure;

measuring, with the shape sensor, a relative orientation between the first coil and a second coil, wherein the second coil is positioned with a second signal wire in a second lumen portion along the sensor longitudinal axis arranged in parallel with the instrument longitudinal axis at a second location along the flexible structure such that the first coil is flexibly coupled to and movable with respect to the second coil as the flexible structure bends and wherein the shape sensor extends between and along the first and second coils; and generating, by control logic, a corrected actuator control signal based on a desired configuration of the flexible structure and the measured shape of the portion of the flexible structure extending from the first location of the first coil toward the distal end of the flexible structure and based on the measured relative orientation between the first coil and the second coil.

12. The method of claim 11, wherein the catheter comprises:
a first catheter section containing the first and second coils; and
a second catheter section adjacent to the first section and extending to the distal tip.

13. The method of claim 11, wherein the control logic determines a six-degree-of-freedom measurement from a first five-degree-of-freedom measurement obtained with the first coil and a second five-degree-of-freedom measurement obtained with the second coil.

14. The method of claim 11, wherein analyzing the electric signal in the first coil comprises determining a global position and orientation at a point along the shape sensor.

15. The method of claim 14, determining the global position and orientation further comprises using a second electrical signal induced in the second coil positioned along the flexible structure.

16. A medical system comprising:
a catheter having a first section and a second section, the second section adjacent to the first section, wherein the catheter defines a longitudinal catheter axis;
a first electromagnetic sensor in a first lumen portion aligned along a longitudinal sensor axis arranged in parallel with the longitudinal catheter axis at a first location along the first section;
a second electromagnetic sensor in a second lumen portion aligned along the longitudinal sensor axis arranged in parallel with the longitudinal catheter axis at a distal end of the first section, the distal end of the first section being adjacent to the second section, wherein the first section between the first location and distal end flexibly couples the first and second electromagnetic sensors so that the first electromagnetic sensor is movable with respect to the second electromagnetic sensor, and wherein the first and second electromagnetic sensors are five-degree-of-freedom sensors; and
a fiber shape sensor system that extends through the first section between and along the first electromagnetic sensor and the second electromagnetic sensor, the fiber shape sensor extending through the second section, the fiber shape sensor system being configured for measurement of a pose of the second section relative to the distal end of the first section and measurement of a relative orientation between the first electromagnetic sensor and the second electromagnetic sensor; and
control logic that receives measurement information from the first and second electromagnetic sensors and the fiber shape sensor and that generates a corrected actuator control signal based on a desired configuration of the catheter and a measured shape of the portion of the catheter extending from the first location toward the distal end of the first section and based on the measured relative orientation between the first electromagnetic sensor and the second electromagnetic sensor.

17. The medical system of claim 16, wherein
the first electromagnetic sensor includes a first coil that has a first magnetic axis oriented at a first angle relative to the longitudinal catheter axis; and
the second electromagnetic sensor includes a second coil has a second magnetic axis that is oriented at a second angle relative to the longitudinal catheter axis, the first and second angles being different such that the second magnetic axis is askew from the first magnetic axis.

18. The medical system of claim 16, wherein the second section is narrower than the first section and the first and second lumen portions are portions of a sensor lumen extending along a length of the first section.

19. The medical system of claim 16, wherein the control logic determines a six-degree-of-freedom measurement from a first five-degree-of-freedom measurement from the first electromagnetic sensor and a second five-degree-of-freedom measurement from the second electromagnetic sensor.

* * * * *